United States Patent
Hardge

[19]
[11] Patent Number: 5,993,428
[45] Date of Patent: Nov. 30, 1999

[54] HEAD COVER WITH EYE SPRAYING CAPABILITY

[76] Inventor: Lawrence Hardge, 3512 Floresta Ave., Los Angeles, Calif. 90230

[21] Appl. No.: 08/947,741

[22] Filed: Oct. 9, 1997

Related U.S. Application Data

[60] Provisional application No. 60/027,715, Oct. 5, 1996.

[51] Int. Cl.⁶ ............................. A61M 7/00; A42B 3/02
[52] U.S. Cl. ............................................ 604/294; 2/422
[58] Field of Search ..................... 604/294, 296, 604/297, 303; 2/410, 6.2, 421, 422

[56] References Cited

U.S. PATENT DOCUMENTS

| | | | |
|---|---|---|---|
| 2,032,101 | 2/1936 | Sullivan . | |
| 2,402,820 | 6/1946 | Kitchen . | |
| 4,193,401 | 3/1980 | Marinello | 604/294 |
| 4,369,782 | 1/1983 | McGee | 128/249 |
| 4,739,905 | 4/1988 | Nelson | 222/145 |
| 4,813,086 | 3/1989 | Davidson | 2/422 |
| 5,807,357 | 9/1998 | Kang | 604/294 |

*Primary Examiner*—Corrine McDermott
*Assistant Examiner*—David J. Cho
*Attorney, Agent, or Firm*—William H. Pavitt, Jr.; David A. Belasco; Mario A. Martella

[57] ABSTRACT

A head covering with eye spraying capability is described. A hard-hat like device incorporates a liquid spraying system between the layers of the head covering for use in environments in which the user may be subject to dirt or dust entering his eyes while working. The invention consists of a digitally activated pump connected by tubing to a reservoir containing water or special eye washing fluid. The reservoir is connected by tubing to one or more spray heads mounted on malleable tubing adjacent the user's face. The tubing supporting the spray heads may be changeably fixed by the user to provide accurate spraying into the user's eyes. A series of one way valves permit air to be replaced in the pump after activation while pressurizing the reservoir and forcing fluid out of the reservoir and through the spray heads and into the user's eyes.

4 Claims, 1 Drawing Sheet

HEAD COVER WITH EYE SPRAYING CAPABILITY

RELATED APPLICATION

This nonprovisional application relates to and claims priority from provisional application Ser. No. 60/027,715 filed Oct. 5, 1996.

FIELD OF THE INVENTION

This invention relates generally to the field of head covers and, particularly, to those head covers in the form of a hard hat or helmet.

DESCRIPTION OF THE PRIOR ART

What are called "hard hats" are employed widely in construction areas, particularly where there is a danger of some object being dropped from above onto a person walking or working below the area from which the object is dropped or falls. Not infrequently, however, those wearing hard hats may encounter dust or some other type of airborne powdered material or chemical which, if it reaches the person's eyes, may cause, at least, a temporary impairment of sight, as well as, great discomfort. Whenever this occurs, it is usually most desirable for the person to be able immediately to wash his eyes with either water or some special eye washing fluid. This was particularly recognized by the inventor of U.S. Pat. No. 4,369,782, which issued on Jan. 25, 1983. As disclosed in that patent, a reservoir of eye washing fluid is provided within the outer wall of the hard hat with ducts leading to spray heads disposed in the eye shield above the eyes. Pressure to force liquid from the reservoir through the ducts to the spray heads is provided by a pumping unit, which is charged up by pumping to provide a desired pressure and the fluid is released through the spray heads upon pulling a release cord.

While apparatus may be constructed in accordance with the teachings of the McGee patent to perform the eye washing functions desired, the presence of the release string in front of the wearer's eyes, may be distracting and annoying and a need for advanced pumping to develop pressure on the reservoir may be objectionable. Also, since the spray heads are located directly above the wearer's eyes, when the spraying occurs, the instantaneous reaction may be to close the eyelids so that the spray does not reach the eyeballs.

These problems with the most pertinent prior art form of hard hat are overcome by the present invention.

SUMMARY OF THE INVENTION

The present invention also contemplates the use of a liquid reservoir within the outer wall of the hard hat, but leading from this reservoir are a pair of bendable plastic tubes terminating in small spray heads. These tubes may be easily bent to dispose the spray heads either laterally adjacent or just below the wearer's eyes, where they may be comfortably seated by providing a small pad surrounding the actual spray head.

At a convenient point on the outside wall of the hard hat, and, preferably centered and disposed just over the hat bill, is a small pump, which may be operated by a thumb or other finger of the wearer's hand. A tube extends from the pump to the reservoir to which it is connected by a one way valve. A further one way valve is provided at the reservoir outlet to each of the flexible plastic tubes.

While the present invention is specifically intended for use with a construction-type hard hat, it could also be incorporated in a bicycle, motorcycle, or racing helmet, or in a military helmet. The invention is most convenient to use, since all that is necessary is to bring up one's hand to the central pump button above the bill and apply sufficient pressure to cause an ejection of fluid from the reservoir into the flexible tubes. Because of the disposition of the spray heads to the side or just below the eyes of the hard hat wearer, it will be found that the eye washing may be effected without the fluid being shut out by the closing of the wearer's eyelids, as is more likely to be the situation where the spray heads are directed from above the eyes.

The present invention, therefore, has considerable utility.

DESCRIPTION OF THE PREFERRED EMBODIMENT

Figure 1:
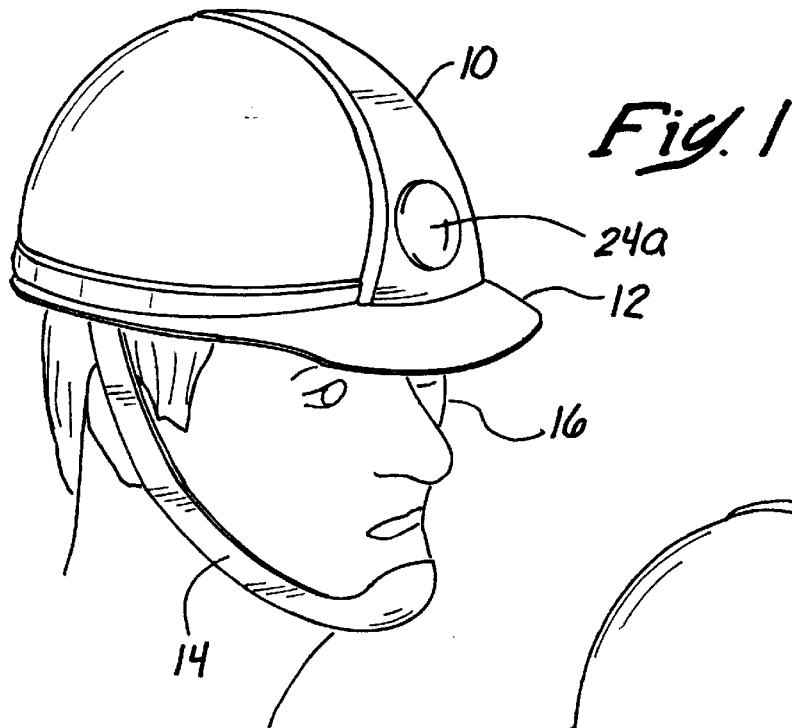
FIG. 1 is a perspective view of a helmet of the present invention on a person's head, with the eye tubes retracted into the helmet and bill.

Referring to the drawings, a hard hat 10, having an eye shielding bill 12 and a chin strap 14 is shown disposed on the head of a construction worker or other person.

Figure 2:
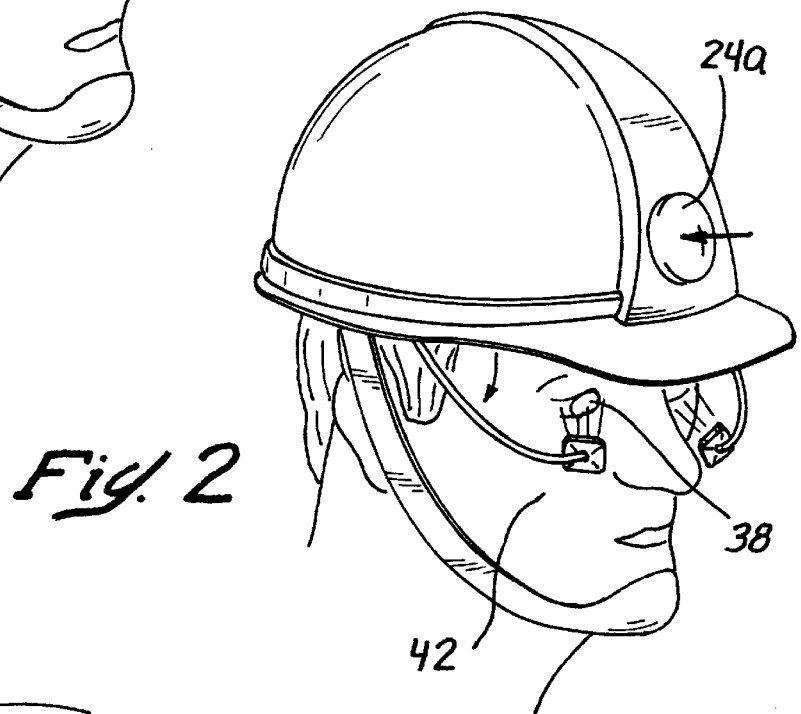
FIG. 2 is a perspective view of the helmet of FIG. 1 showing the eye flushing tubes and their spray dispensers positioned below the wearer's eyes.
Figure 3:
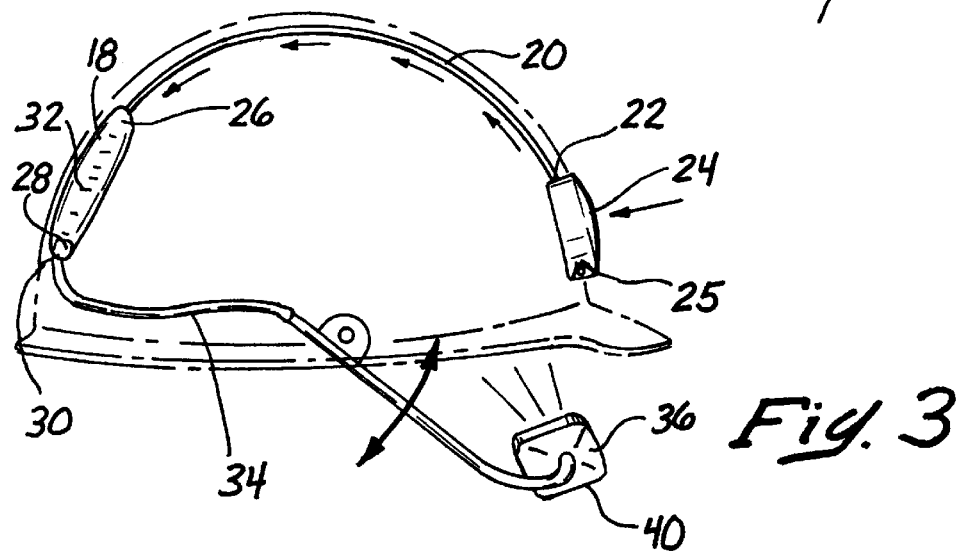
FIG. 3 is a side elevation of the helmet shown in FIG. 2, partly in section.

As best seen in FIG. 3, a fluid reservoir 18 is connected by a first tube 20 to the outlet 22 of an air pump 24. The face of the air pump 24 may be in the form of a large button 24a. A one way valve 25 is provided to enable the pump 24 to refill with air after the button 24a has been pushed in to provide air pressure into the tube 20. A second one way valve 26 is provided at the point where the first tube 20 is connected to the reservoir so that, when air under pressure passes from the pump 24 to the reservoir 18, the one way valve 26 opens. Similarly, a one way valve 28 is provided at each of the two outlets 30 of the reservoir 18. The reservoir 18 is initially filled with water or a special eye washing fluid. The outlets 30 of the reservoir 18 are actually bifurcated to allow a second tube 34, provided on each side of the helmet 10 to extend from its connecting outlet 30 over the wearer's temple to terminate in a spray head 36. The second tube 34, desirably, should be of a plastic, which may be flexible, yet hold itself in whatever disposition it is last received by manual bending. Thereby, the spray head 36 may be most advantageously placed with reference to the wearer's eye 38, as shown in FIG. 2. The spray head 36 may be comprised of a small circular or rectangular base 40, which may be placed almost in abutment with the wearer's cheek 42.

In use, then, the helmet may be worn in the manner shown in FIG. 1, with the spray head and tube retracted until a situation develops where there is some likelihood that the wearer of the hard hat may encounter dust or some other airborne pollutant, which could enter his eyes. At that point, the tubes 34 on each side of the hat may be bent down and in such a manner as to position the spray heads 36 as shown in FIG. 2. When an eye washing spray is needed, the wearer simply pushes the button 24a to institute pumping of the fluid 32 from the reservoir 18 through the second tubes 34 to the spray head 36. When the pumping ceases, the one way valve 22, which opened under pressure, and the one way valves 26 and 28, all close until the next air pressure burst, at which time they will reopen to dispense fluid through the second tubes 34 and out of the spray heads 36.

Water or a special eye washing fluid can be placed into the reservoir at the point where the first tube attaches to the reservoir by detaching the first tube. Also, water or a special eye washing fluid can be placed into the reservoir at either of the two outlets by detaching the corresponding second tube.

It may be seen, then, that the present invention provides a hard hat with excellent eye washing capability, which may be activated by the wearer pushing the button pump disposed centrally above the bill 12 of the hard hat.

I claim:

1. A head cover with eye spraying capability, comprising:
    a head cover;
    a pump, said pump being activatable by application of pressure with a user's finger;
    a reservoir;
    at least one spray head directed towards a user's face;
    first tubing connecting said pump to said reservoir;
    second tubing connecting said reservoir to said spray head and being positioned so that the spray head is disposed no higher than laterally adjacent the user's eye;
    means for attaching said pump, said reservoir, and said first tubing and second tubing to said head cover; and,
    a liquid selected from the group consisting of water and special eye washing fluid, disposed within said reservoir.

2. The head cover with eye spraying capability as described in claim 1, wherein the pump further comprises:
    an activating button; and
    a first one way valve enabling the pump to refill with air after activation.

3. The head cover with eye spraying capability as described in claim 2, wherein the reservoir further comprises:
    an inlet orifice;
    a second one way valve disposed at said inlet orifice providing valving between the pump and the reservoir;
    an outlet orifice; and
    a third one way valve disposed at said outlet orifice providing valving between the reservoir and the spray head.

4. The head cover with eye spraying capability as described in claim 1, wherein the tubing connecting the reservoir to the spray head is formed of a malleable material allowing said tubing to retain the shape to which it is changeably fixed by the user to effect accurate spraying into the user's eyes.

* * * * *